United States Patent

Stridde

[11] 4,075,126
[45] * Feb. 21, 1978

[54] CATALYST FOR ALKYLATING AROMATIC HYDROCARBONS

[75] Inventor: George E. Stridde, Houston, Tex.

[73] Assignee: N L Industries, Inc., New York, N.Y.

[*] Notice: The portion of the term of this patent subsequent to June 22, 1993, has been disclaimed.

[21] Appl. No.: 739,331

[22] Filed: Nov. 5, 1976

Related U.S. Application Data

[60] Continuation-in-part of Ser. No. 671,507, March 29, 1976, Pat. No. 3,992,467, which is a division of Ser. No. 503,985, Sept. 6, 1974, Pat. No. 3,965,043.

[51] Int. Cl.² .................... B01J 29/06; B01J 29/00
[52] U.S. Cl. ............................ 252/455 R; 252/457; 252/458; 252/459; 252/460
[58] Field of Search ............... 252/455 R, 457, 458, 252/459, 460; 260/671 C

[56] References Cited

U.S. PATENT DOCUMENTS

| | | | |
|---|---|---|---|
| 3,852,405 | 12/1974 | Granquist | 252/455 R |
| 3,855,147 | 12/1974 | Granquist | 252/455 R |
| 3,965,043 | 6/1976 | Stridde | 252/455 R |

Primary Examiner—Carl F. Dees

[57] ABSTRACT

Alkylatable aromatic hydrocarbons are alkylated with olefins and alkylhalides under anhydrous alkylating conditions in the presence of a metallic cation exchanged trioctahedral 2:1 layer-lattice smectite-type catalyst in which the metallic cation has a Pauling electronegativity greater than 1.0. In a specific embodiment, there is provided a catalyst comprising a trioctahedral smectite-type clay having the structural formula:

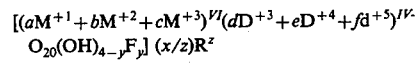

$$[(aM^{+1}+bM^{+2}+cM^{+3})^{VI}(dD^{+3}+eD^{+4}+fd^{+5})^{IV}O_{20}(OH)_{4-y}F_y] (x/z)R^z$$

wherein the cations M are in the central octahedral layer and have an ionic radius not greater than 0.75A, the cations D are in the two outer tetrahedral layers and have an ionic radius not greater than 0.64A, R is at least one metallic cation having a Pauling electronegativity greater than 1.0, such as $Al^{3+}$, $In^{3+}$, and $Cr^{3+}$ in cation exchange positions on the surface of the clay platelets, and wherein $11 \leq a+2b+3c \leq 12.3$
$31 \leq 3d+4e+5f \leq 32$
$43 \leq a+2b+3c+3d+4e+5f \leq 43.67$
$x = 44 - (a+2b+3c+3d+4e+5f)$
$0 \leq y \leq 4$
$0 \leq a \leq 1$
$5 \leq b \leq 6$
$0 \leq c \leq 0.3$
$0 \leq d \leq 1$
$7 \leq e \leq 8$
$0 \leq f \leq 0.4$ provided that when $a=0$, then either: (1) $f>0$; or (2) $c>0$ and $M^{+3}$ and $D^{+3}$ are not $Al^{+3}$ when $M^{+2}$ is 100 mole percent Mg.

30 Claims, No Drawings

CATALYST FOR ALKYLATING AROMATIC HYDROCARBONS

This application is a continuation-in-part of copending application Ser. No. 671,507 filed Mar. 29, 1976, now U.S. Pat. No. 3,992,467 which is a division of application Ser. No. 503,985 filed Sept. 6, 1974, now U.S. Pat. No. 3,965,043.

This invention relates to a catalyst for the liquid phase alkylation of aromatic hydrocarbons which comprises certain cation-exchanged trioctahedral 2:1 layer-lattice smectite-type clays. More particularly, the present invention provides a catalyst which comprises certain trioctahedral 2:1 layer-lattice smectite-type clay minerals which have a metal cation having a Pauling electronegativity greater than 1.0 in ion-exchange positions on the surface of the clay particles.

It has been reported that various materials containing acidic catalytic sites are useful in catalyzing the reaction between aromatic hydrocarbons and various alkylating agents such as olefins and alkylhalides. See for example: the Kirk-Othmer Encyclopedia of Chemical Technology, 2nd Edition, Vol. 1, pp. 882-901 (1963); "Alkylation of Benzene with Dodecene-1 Catalyzed by Supported Silicotungstic Acid," R. T. Sebulsky and A. M. Henke, Ind. Eng. Chem. Process Res. Develop., Vol. 10, No. 2, 1971, pp. 272-279; "Organic Molecule and Zeolite Crystal: At the Interface," P. B. Venuto, Chem. Tech., April 1971, pp. 215-224; "Catalysis by Metal Halides. IV. Relative Efficiencies of Friedel-Crafts Catalysts in Cyclohexane-Methylcyclopentane Isomerization, Alkylation of Benzene and Polymerization of Styrene," G. A. Russell, J. Am. Chem. Soc., Vol. 81, 1959, pp. 4834-4838.

It has also been proposed to use various modified clays as catalysts in various acid catalyzed reactions such as alkylation, isomerization, and the like. See for example the following U.S. Pat. Nos.: 3,665,778; 3,665,780; 3,365,347; 2,392,945; 2,555,370; 2,582,956; 2,930,820; 3,360,573; 2,945,072; 3,074,983. Other references which disclose the use of clays as catalysts are as follows: "Acid Activation of Some Bentonite Clays," G. A. Mills, J. Holmes and E. B. Cornelius, J. Phy. & Coll. Chem., Vol. 54, pp. 1170-1185 (1950); "H-Ion Catalysis by Clays," N. T. Coleman and C. McAuliffe, Clays and Clay Minerals, Vol. 4, pp. 282-289 (1955); "Clay Minerals as Catalysts," R. H. S. Robertson, Clay Minerals Bull., Vol. 1, No. 2, pp. 47-54 (1948); "Catalytic Decomposition of Glycerol by Layer Silicates", G. F. Walker, Clay Minerals, Vol. 7, pp. 111-112 (1967); "Styrene Polymerization with Cation-Exchanged Aluminosilicates," T. A. Kusnitsyna and V. M. Brmolko, Vysokomol. Soedin., Ser. B1968, Vol. 10, No. 10, pp. 776-9 - see Chem. Abstracts 70:20373x (1969); "Reactions Catalyzed by Minerals. Part I. Polymerization of Styrene," D. H. Solomon and M. J. Rosser, J. Applied Polymer Science, Vol. 9, 1261-1271 (1965).

I have found that trioctahedral 2:1 layer-lattice smectite-type minerals which have had their exchangeable cations replaced with metallic cation having a Pauling electronegativity greater than 1.0 are effective catalysts for the alkylation of an alkylatable aromatic hydrocarbon, e.g. benzene, with an olefin or alkylhalide under anhydrous alkylating conditions in the liquid phase.

Accordingly, it is an object of this invention to provide a catalyst for alkylating in the liquid phase an alkylatable aromatic hydrocarbon with an olefin or alkylhalide under anhydrous alkylating conditions. It is another object of this invention to provide a catalyst comprising certain metallic cation exchanged trioctahedral 2:1 layer-lattice smectite-type minerals wherein the metallic cations has a Pauling electronegativity greater than 1.0. Other objects and advantages of this invention will become apparent to those skilled in the art upon reading the disclosure and the appended claims.

The catalyst of this invention comprises (1) a metallic cation, designated R herein, which has a Pauling electronegativity greater than 1.0 exchanged onto the surface of (2) certain trioctahedral 2:1 layer-lattice smectite-type minerals as disclosed herein.

Representative metallic cations which are useful in this invention may be derived from the following metals, the Pauling electronegativity of which is given in parentheses (See "The Nature of The Chemical Bond," L. Pauling, 1960, 3rd Edition); Be(1.5), Mg (1.2), Al (1.5), Ga (1.6), In (1.7), Cu (1.9), Ag (1.9), La (1.1), Hf (1.3), Cr (1.6), Mo (1.8), Mn (1.5), Fe (1.8), Ru (2.2), Os (2.2), Co (1.8), Rh (2.2), Ir (2.2), Ni (1.8), Pd (2.2), Pt (2.2), and Ce (1.1). Mixtures of two or more metallic cations having a Pauling electronegativity greater than 1.0 may be present in the catalyst in cation exchange positions on the surface of the trioctahedral 2:1 layer-lattice smectite-type mineral.

The structure of trioctahedral 2:1 layer-lattice smectite minerals is well known. See for example the following publications, incorporated herein by reference: "The Chemistry of Clay Minerals," C. E. Weaver and L. D. Pollard, 77-86 (1973). Elsevier Scientific Publishing Co.; "Clay Mineralogy," R. E. Grim, 77-92, 2nd Edition (1968). McGraw-Hill Book Co.; "Silicate Science, Vol. 1. Silicate Structure," W. Eitel, 234-247 (1964). Academic Press; "Rock-Forming Minerals, Vol. 3. Sheet Silicates," W. A. Deer, R. A. Howie, and J. Zussman, 226-245 (1962). John Wiley and Sons, Inc.

2:1 layer-lattice clay minerals contain a central layer of cations octahedrally coordinated to oxygen and hydroxyl anions which are linked through shared oxygen anions to two layers of cations tetrahedrally coordinated to oxygen and hydroxyl anions, one on each side of the central octahedral layer. Fluorine may substitute for the hydroxyl groups. For each unit cell of such clays there are 6 octahedral cation sites and 8 tetrahedral cation sites. The sum of the cationic charges for electroneutrality of the layer-lattices is 12 for the octahedral cation sites and 32 for the tetrahedral cation sites. Thus the 6 octahedral cation sites can be filled with 6 divalent (+2) cations which satisfies the required layer charge. Clays which contain approximately 6 octahedrally coordinated cations are called trioctahedral. The theoretical formula without considering lattice substitutions for trioctahedral 2:1 layer-lattice clay minerals is $[(M^{+2}_6)^{VI}(D^{+4}_8)^{IV}O_{20}(OH)_4]n\ H_2O$ (interlayer water). The number of cations in the octahedral layer of naturally occurring trioctahedral 2:1 layer-lattice clay minerals is within the range from 5.76 to 6.00. However, the 6 octahedral cation sites can also be filled with 4 trivalent (+3) cations which satisfies the required layer charge. Such clays which contain approximately 4 octahedrally coordinated cations are called dioctahedral. The theoretical formula without considering lattice substitutions for dioctahedral 2:1 layer-lattice clay minerals is $[(M^{+3}_4)^{VI}(D^{+4}_8)^{VI}O_{20}(OH)_4] \cdot nH_2O$ (interlayer water). The number of cations in the octahedral layer of naturally occurring dioctahedral 2:1 layer-lattice clay minerals is within the range from 4.00 to 4.44.

The octahedrally coordinated cation sites can accommodate cations which have an ionic radius not greater than 0.75 A and the tetrahedrally coordinated cation sites can accommodate cations which have an ionic radius not greater than 0.64 A. Thus various cations can isomorphously substitute for the divalent cations in the central octahedral layer of trioctahedral clays, for the trivalent cations in the central octahedral layer of dioctahedral minerals, and for the tetravalent cations in the outer tetrahedral layers of both types of minerals. Such substitutions give rise to a charge imbalance within the octahedral and tetrahedral layers in which the substitution occurs. The charge imbalance usually results from the substitution of a cation with a smaller cation charge thus creating a negatively charged layer-lattice. This negative charge is neutralized by cations on the surface of the layer lattices.

The smectite-type minerals useful in this invention can be synthesized hydrothermally. In general a gel containing the required molar ratios of silica, alumina, magnesia and fluoride and having a pH at least 8 is hydrothermally treated at a temperature within a range from 100° – 350° C, preferably 250° – 300° C, and preferably at the autogenous water vapor pressure for a period of time sufficient to crystallize the desired smectite, generally 12–72 hours depending on the temperature of reaction. In general as the reaction temperature decreases the reaction time increases for well crystallized smectite-type minerals. Many of the smectite-type minerals can be crystallized from melts of the oxides at very high temperatures, generally greater than 950° C.

The following references incorporated herein by reference, describe processes for the hydrothermal synthesis of smectite-type minerals: "A Study of the Synthesis of Hectorite," W. T. Granquist and S. S. Pollack. Clays and Clay Minerals, Proc. Nat'l. Conf. Clays Clay Minerals. 8, 150-169 (1960); "Synthesis of a Nickel-Containing Montmorillonite," B. Siffert and F. Dennefeld. C. R. Acad. Sci., Paris, Ser. D. 1968, 267 (20), 1545-8 (Reference Chemical Abstracts, Vol. 70; 43448q); "Synthesis of Clay Minerals," S. Caillere, S. Henin, and J. Esquevin. Bull. Groups franc-argiles, 9, No. 4, 67–76 (1957) (Reference Chemical Abstracts 55:8190e); U.S. Pat. No. 2,658,875; U.S. Pat. No. 3,586,478; U.S. Pat. No. 3,666,407; U.S. Pat. No. 3,671,190; U.S. Pat. No. 3,844,978; U.S. Pat. No. 3,844,979.

As indicated, the trioctahedral 2:1 layer-lattice smectite-type clay minerals useful in preparing the catalysts for the catalytic processes described and hereinafter claimed can be prepared synthetically by either a hydrothermal process or a pneumatolytic process. Such smectite-type clays can be synthesized having one or more metallic cations having an ionic radius not greater than 0.75A in the central octahedral layer and having one or more metallic cations having an ionic radius not greater than 0.64A in the two outer tetrahedral layers. Thus such synthetic trioctahedral 2:1 layer-lattice smectite-type clays have the following general structural formula:

$$[(aM^{+1} + bM^{+2} + cM^{+3})^{VI}(dD^{+3} + eD^{+4} + fD^{+5})^{IV} O_{20}(OH)_{4-y}F_y](x/z)G^z \quad (I)$$

where
$11 \leq a + 2b + 3c \leq 12.3$
$31 \leq 3d + 4e + 5f \leq 32$
$43 \leq a + 2b + 3c + 3d + 4e + 5f \leq 43.67$
$x = 44 - (a + 2b + 3c + 3d + 4e + 5f)$ $0 \leq y \leq 4$
$0 \leq a \leq 1$
$5 \leq b \leq 6$
$0 \leq c \leq 0.3$
$0 \leq d \leq 1$
$7 \leq e \leq 8$
$0 \leq f \leq 0.4$ provided that when $a = 0$, then either: (1) $f > 0$; or (2) $c > 0$ and $M^{+3}$ and $D^{+3}$ are not $Al^{3+}$ when $M^{+2}$ is 100 mole percent Mg, and where the cations M are in the octahedral layer and have an ionic radius not greater than 0.75A, the cations D are in the two outer tetrahedral layers and have an ionic radius not greater than 0.64A, and G is at least one exchangeable charge-balancing cation of valence $z$.

Preferably the cation M is selected from the group consisting of $Li^+$, $Mg^{+2}$, $Ni^{2+}$, $Co^{2+}$, $Zn^{2+}$, $Cu^{2+}$, $Mn^{2+}$, $Al^{3+}$, $Cr^{+3}$, and mixtures thereof, the cation D is selected from the group consisting of $Al^{3+}$, $Cr^{3+}$, $Fe^{3+}$, $Si^{+4}$, $Ge^{+4}$, $P^{+5}$, $V^{+5}$, and mixtures thereof, and the cation G is selected from the group consisting of $Li^+$, $Na^+$, $NH_4^+$, and mixtures thereof, unless G is a cation having a Pauling electronegativity greater than 1.0. Most preferably the cation $M^{+2}$ contains less than 100 mole % $Mg^{2+}$, i.e., $Mg^{2+} < b$.

The catalyst of the present invention can be prepared by an ion-exchange process wherein a metallic cation having a Pauling electronegativity greater than 1.0 can be made to replace the exchangeable cation of the smectite-type clay. Preferably an aqueous solution of a soluble salt of the desired metallic cation is admixed with the desired smectite-type clay for a period of time sufficient to effect the desired exchange. Preferably an amount of metallic cation will be used which is from 100% to 500% of the exchange capacity of the smectite-type clay, more preferably 100% to 300%. It is preferred to exchange 100% of the exchangeable cations of the smectite with the metallic cations of this invention. It is also preferred to remove excess metallic cation salt and the soluble salt by-products of the exchange from the catalyst such as by filtration and washing prior to drying the catalyst. Alternatively the excess metallic cations salt and soluble salt by-product can be removed from the dried catalyst by slurrying the catalyst in an appropriate solvent, such as water or methanol, followed by filtration and re-drying. The exchange can also be conducted using a solution of the metallic cation salt in an appropriate organic solvent, such as methanol. Alternatively, the process disclosed in U.S. Pat. No. 3,725,528 can be used to prepare the catalyst.

The catalyst of this invention has the general structural formula:

$$[(aM^+ + bM^{+2} + cM^{+3})^{VI}(dD^{+3} + eD^{+4} + fD^{+5})^{IV} O_{20}(OH)_{4-y}F_y](x/z)R^{+z}$$

where M, D, $x$, $y$, $a$, $b$, $c$, $d$, $e$, $f$ and the relationships therebetween are as described previously in connection with formula (I) since they are not changed by the cation exchange process, and where R is the metallic cation having a Pauling electronegativity greater than 1.0 of valence $z$. Preferably when $0 < a \leq 1$, then either $0 \leq d \leq 1$ or $0 \leq f \leq 0.4$ or $0 \leq c \leq 0.3$. Preferably $0 \leq f \leq 0.4$ when $a = 0$. Thus representative of the catalysts of this invention are the following metallic cation exchanged synthetic trioctahedral smectite-type clays:

$$[(Ni_3Mg_3)^{VI}(Si_7Al_{0.75}V_{0.25})^{IV}O_{20}(OH)_4](0.5/z)\,R^z$$

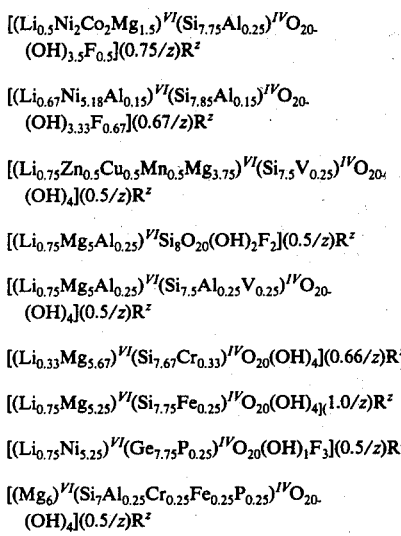

The catalyst of this invention has been found to be active in catalyzing the reaction between alkylatable aromatic hydrocarbons and olefin-acting compounds under anhydrous alkylating conditions in the liquid phase.

Alkylatable aromatic hydrocarbons which can be used in the inventive process include benzene, toluene, xylene, the naphthalene series of hydrocarbons, etc. Any aromatic hydrocarbon can be alkylated if it has an unsubstituted carbon as long as steric hindrance does not prevent alkylation with the particular olefin-acting compound chosen for use in the process, and as long as the alkyl side chains on the aromatic ring do not prevent the aromatic compound from being absorbed onto the layer-lattice surfaces of the catalyst. Benzene is the preferred aromatic hydrocarbon.

The olefin-acting compounds may be selected from the group consisting of mono-olefins, alkyl bromides, alkyl chlorides, and mixtures thereof. Representative olefins include ethylene, propylene, 1-butene, 2-butene, 1-pentene, 2-pentene, 1-hexane, propylene tetramer, 1-octadecene, etc. Representative alkylhalides include n-butyl bromide, n-butyl chloride, n-dodecyl bromide, n-dodecyl chloride, etc.

The process is carried out in the liquid phase utilizing a catalytically effective amount of the catalyst hereinbefore described. The catalyst can be used in amounts from 1% to 100% by weight based on the olefin-acting compound depending on the particular metallic cation-exchanged smectite-type catalyst chosen for the reaction, the temperature of the reaction, and the length of time the catalyst has been in service. Preferably a concentration of catalyst from 2% to 50% by weight is used since this gives a relatively fast alkylation, still more preferably 2% to 10%.

The pressure can be elevated and is not critical as long as some of the olefin-acting compound can be kept dissolved in the liquid aromatic phase. Thus the pressure should be correlated with the temperature at which the reaction is carried out in order to maintain the aromatic hydrocarbon in the liquid phase and to maintain a sufficient amount of olefin-acting compound dissolved therein to allow the alkylation reaction to proceed. Atmospheric pressure is preferred because of the simplicity of operations under atmospheric conditions.

The process is conducted at an elevated temperature since the rate of alkylation is undesirably low at room temperature. Preferably the temperature is in the range from 40° C to 200° C, more preferably 70° C to 150° C. It is desirable to conduct the process at the boiling point (reflux temperature) of the alkylatable aromatic hydrocarbon provided that it is in the above noted range. A non-alkylatable solvent such as cyclohexane, can be used to provide the liquid alkylating medium and the temperature can conveniently be maintained at the boiling point of the solvent.

The molar ratio of alkylatable aromatic hydrocarbon to alkylating agent, i.e., the olefin-acting compound, can vary widely depending on the product desired. Thus at higher ratios such as 10 or above essentially only mono-alkylated product is obtained whereas at lower ratios the amount of polyalkylated product is increased. Preferably a molar ration within the range from 3.1 to 20:1 will be used more preferably 5:1 to 10:1.

It is important to maintain the reaction system free of water since water has a deactivating effect on the catalyst. Thus the catalyst must be dried before use. This may conveniently be done by removing the water from the catalyst at a low temperature, i.e., less than about 200° C. Alternatively the water may be removed by azeotropic distillation from a mixture of the catalyst in the alkylatable aromatic hydrocarbon or the solvent to be used in the reaction. This method will also remove any water present in these organic systems and is preferred. The term "anhydrous" as used in this specification and in the claims is intended to mean that any free water which is present in the catalyst or the organic components present in the reaction mix is removed from the reaction system.

The following non-limiting examples are given in order to illustrate the invention.

EXAMPLES 1 – 27

Various cation exchanged forms of the natural mineral hectorite was prepared as follows: The exchange cation salt was dissolved in 500 to 750 ml. of methanol. Hectorite clay which had been previously dispersed in water, centrifuged, and spray dried in order to obtain the purified clay, was mixed in this salt solution at a concentration of 300 milliequivalents of cation per 100 grams of clay. This mixture was allowed to stand for approximately 20 hours before it was filtered. The filter cake was re-dispersed in 500 – 750 ml. of methanol followed by filtration for a total of 3 successive washings. The cation exchanged hectorite was then air dried for 20 hours at room temperature followed by oven drying at 105° C for 2 hours. The clay obtained by this process was very fine and needed no grinding. In the case of $Ag^+$-hectorite, 10 ml. of concentrated nitric acid was added to the methanol solution before adding the clay to the solution, in order to prevent oxide formation or hydrolysis of the $Ag^+$.

These cation exchanged hectorite clays were evaluated as catalysts for the alkylation of benzene using the following procedure: 10 grams of the cation exchanged hectorite and 200 – 250 ml. of benzene are refluxed in a round bottom flask equipped with a Dean-Stark tube attached to remove, azeotropically, sorbed water from the clay. After 2 – 4 hours the tube was removed and the reflux condenser rinsed with methanol and air dried to remove any residual moisture trapped in the condenser. 10 grams of the alkylating agent were added to the flask and the mixture refluxed with stirring for 24 hours. The clay was removed by filtration and washed with 100 ml. of benzene. The benzene was removed from the filtrate by vacuum evaporation leaving a product of unreacted alkylating agent and/or alkylbenzene.

This product was then weighed and analyzed by either infrared spectrophotometry, refractometry, or gas chromatography to determine the amount of alkylbenzene formed. The cation exchanged hectorites evaluated and the data obtained are given in Table 1.

The data indicate that the natural hectorite clay containing exchanged metallic cations having a Pauling electronegativity less than or equal to 1.0 were ineffective as catalysts for the alkylation of benzene. Metallic cations having a Pauling electronegativity greater than 1.0 were effective catalysts when exchanged onto hectorite. These include $Be^{2+}$ and $Mg^{2+}$ (Group IIA), $Al^{3+}$ and $In^{3+}$ (Group IIIA), $La^{3+}$ (Group III), $Cr^{3+}$ (Group VIA), $Mn^{2+}$ (Group VIIB), $Fe^{3+}$, $Co^{2+}$, $Ni^{2+}$ and $Pd^{2+}$ (Group VIII), $Cu^{2+}$ and $Ag^+$ (Group IB), and $Ce^{3+}$ (rare earths). The effect of moisture within the reaction zone on the activity of certain of the catalysts can be ascertained by reference to the data for Examples 1, 4 and 6. The small amount of water which remained in the reflux condenser (Examples 1,6) or in the atmosphere (Example 4) was sufficient to decrease the activity of $Al^{3+}$-exchanged hectorite approximately 50%, whereas $In^{3+}$-exchanged hectorite was very active in the presence of such small quantities of water.

TABLE 1

Alkylation of Benzene
Alkylating Agent: Catalyst Weight Ratio = 1:1
Benzene: Alkylating Agent Mole Ratio = 10:1
Temperature = 80.1° C (B.P. of Benzene)
Duration of Reaction = 24 Hours
Catalyst = Various Cation Exchanged Forms of Hectorite

| Ex. | Exchangeable Cation on Hectorite | Pauling Electronegativity of Cation | Alkylating Agent | % Yield of Alkylbenzene |
|---|---|---|---|---|
| 1  | $Al^{3+}$ | 1.5 | n-Butyl Bromide  | 80 (36)[a] |
| 2  | $In^{3+}$ | 1.7 | n-Butyl Bromide  | 86 |
| 3  | $H^+$     | 2.1 | n-Butyl Bromide  | 10 |
| 4  | $Al^{3+}$ | 1.5 | n-Butyl Chloride | 18 (40)[b] |
| 5  | $In^{3+}$ | 1.7 | n-Butyl Chloride | 94 |
| 6  | $Al^{3+}$ | 1.5 | Lauryl Bromide   | 89 (48)[a] |
| 7  | $In^{3+}$ | 1.7 | Lauryl Bromide   | (86)[a] |
| 8  | $Fe^{3+}$ | 1.8 | Lauryl Bromide   | (31)[a] |
| 9  | $Al^{3+}$ | 1.5 | 1-Octadecene     | 93[c] |
| 10 | $In^{3+}$ | 1.7 | 1-Octadecene     | 93[d] |
| 11 | $Al^{3+}$ | 1.5 | 1-Dodecene       | 88 |
| 12 | $Fe^{3+}$ | 1.8 | 1-Dodecene       | 88 |
| 13 | $Cr^{3+}$ | 1.6 | 1-Dodecene       | 100 |
| 14 | $La^{3+}$ | 1.1 | 1-Dodecene       | 100 |
| 15 | $Ce^{3+}$ | 1.1 | 1-Dodecene       | 99 |
| 16 | $Be^{2+}$ | 1.5 | 1-Dodecene       | 96 |
| 17 | $Mg^{2+}$ | 1.2 | 1-Dodecene       | 96 |
| 18 | $Mn^{2+}$ | 1.5 | 1-Dodecene       | 92 |
| 19 | $Co^{2+}$ | 1.8 | 1-Dodecene       | 91 |
| 20 | $Ni^{2+}$ | 1.8 | 1-Dodecene       | 93 |
| 21 | $Cu^{2+}$ | 1.9 | 1-Dodecene       | 99 |
| 22 | $Pd^{2+}$ | 2.2 | 1-Dodecene       | 71 |
| 23 | $Ag^+$    | 1.9 | 1-Dodecene       | 100 |
| 24 | $Ca^{2+}$ | 1.0 | 1-Dodecene       | 52 |
| 25 | $Ba^{2+}$ | 0.9 | 1-Dodecene       | 5 |
| 26 | $Li^+$    | 1.0 | 1-Dodecene       | 5 |
| 27 | $Na^+$    | 0.9 | 1-Dodecene       | Trace[e] |

[a]Methanol Rinse of Reflux Condenser Omitted
[b]Nitrogen Circulated through the Reaction Flask
[c]Small Amount of n-Butyl Bromide Added to Promote the Reaction
[d]Small amount of Lauryl Bromide added to promote the reaction
[e]Clay without Exchange Treatment - Primarily $Na^+$ Form.

EXAMPLES 28 – 43

Several cation exchanged hectorites were prepared by at least one of the following procedures as indicated in Table 2: Process A — exchange in methanol solution as in Examples 1 - 27; Process B — exchange in aqueous solution substituting water for methanol in Process A except in the last washing step; Process C — exchange in aqueous solution, no washing. These catalysts were evaluated for the alkylation of benzene by 1-dodecene at a 1-dodecene:catalyst weight ratio of 10:1 using the same process as in Examples 1–27. The percent conversion of the olefin after one hour is given in Table 2. The catalysts used in Examples 33, 34, 37 and 38 were the same catalysts used in Examples 32, 33, 36 and 37 respectfully, after rinsing them with benzene.

The data indicate that water is the preferred solvent for the metallic cation salt, i.e., for the exchange solution, and that the catalyst should be washed to remove soluble salts from the catalyst. The catalyst can be re-used after rinsing with benzene to remove adsorbed products from the catalyst.

TABLE 2

Alkylation of Benzene with 1-Dodecene
Benzene: 1-Dodecene Mole Ratio = 10:1
1-Dodecene: Catalyst Weight Ratio = 10:1
Temperature = 80.1° C (B.P. of Benzene)
Duration of Run = One Hour

| Ex. | Exchangeable Cation on Hectorite | 1-Dodecene to Cation Ratio | Catalyst Preparation Process | % Conversion of Olefin |
|---|---|---|---|---|
| 28 | $Al^{3+}$ | 1,000/1 | A | 53 |
| 29 | $Al^{3+}$ | 1,000/1 | B | 95 |
| 30 | $Al^{3+}$ | 1,000/1 | C | 1.2 |
| 31 | $Al^{3+}$ | 1,000/1 | C | 4.4 |
| 32 | $Al^{3+}$ | 1,000/1 | B | 97 |
| 33 | $Al^{3+}$ | 1,000/1 | B | 77[a] |
| 34 | $Al^{3+}$ | 1,000/1 | B | 37[b] |
| 35 | $Cr^{3+}$ | 526/1 | A | 90 |
| 36 | $Cr^{3+}$ | 526/1 | B | 99+ |
| 37 | $Cr^{3+}$ | 526/1 | B | 82[c] |
| 38 | $Cr^{3+}$ | 526/1 | B | 58[d] |
| 39 | $In^{3+}$ | 263/1 | A | 3 |
| 40 | $In^{3+}$ | 263/1 | B | 99 |
| 41 | $Mg^{2+}$ | 833/1 | A | 29 |
| 42 | $Fe^{3+}$ | 357/1 | B | 84 |
| 43 | $Ag^+$    | 256/1 | A | 21 |

[a]The catalyst from the previous experiment, after X hours reaction time and Y% conversion of dodecene, was re-used after it was rinsed with benzene, where X = 4 hours and Y = 99.3%.
[b]As (a), except X = 7 hours and Y = 99.1%.
[c]As (a), except X = 1 hours and Y = 99+%.
[d]As (a), except X = 3 hours and Y = 93.4%.

EXAMPLE 44

A sample of synthetic hectorite, commercially available from N L INDUSTRIES, INC. as BARASYM ® LIH, was exchanged with $AlCl_3$ using the process of Examples 1 – 27 to the $Al^{3+}$-exchanged form. This sample was used to catalyze the reaction between n-butyl bromide and benzene using the same process and conditions as in Examples 1 – 27. 62% of this alkylating agent were converted to alkylbenzene.

EXAMPLE 45

A sample of synthetic $Na^+$-stevensite was exchanged to the $Al^{3+}$ form with $AlCl_3$ using the aqueous exchange process B of Examples 28 – 43. This $Al^{3+}$-stevensite was characterized by the structural formula:

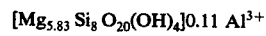

$[Mg_{5.83} Si_8 O_{20}(OH)_4]0.11\ Al^{3+}$

This sample was evaluated as a catalyst for the conversion of 1-dodecene and benzene to dodecylbenzene as in Examples 28 – 43. 44% of the dodecene was converted to dodecylbenzene after 1 hour.

EXAMPLES 46 –47

$Al^{3+}$-exchanged hectorite was used to catalyze the alkylation of anthracene with 1-octadecene by refluxing anthracene and 1-octadecene in a molar ratio of 10:1 and an octadecene:catalyst ratio of 1:1 in cyclohexane. No octadecene was detectable after 24 hours. Similar results were obtained when biphenyl was substituted for the anthracene.

EXAMPLE 48

A sample of synthetic Na$^+$-saponite containing occluded MgO was exchanged with AlCl$_3$ using the process of Example 44. The Al$^{3+}$-saponite is characterized by the structural formula:

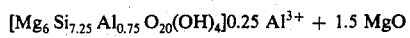
[Mg$_6$ Si$_{7.25}$ Al$_{0.75}$ O$_{20}$(OH)$_4$]0.25 Al$^{3+}$ + 1.5 MgO This sample was evaluated as in Examples 28 - 43. 74% of the dodecene was converted to dodecylbenzene after 1 hour.

EXAMPLES 49 - 59

An Al$^{3+}$-exchanged hectorite and a Cr$^{3+}$-exchanged hectorite (purified natural clay as in Examples 1 - 27) were prepared by the aqueous exchange process B of Examples 28 - 43. These clays were evaluated as catalysts for the alkylation of benzene by 1-dodecene at various mole ratios of benzene to dodecene and/or various weight ratios of dodecene to catalyst as indicated in Table 3. The percent conversion of dodecene after 1 hour and, in some cases, 24 hours using the same process as in Examples 1 -27 was determined. The data obtained are given in Table 3.

The data indicate that these exchanged clays were excellent catalysts at concentrations of exchanged clay greater than about 2%, based on the weight of dodecene, although concentrations as low as 1% converted most of the dodecene in 24 hours.

Table 3

Alkylation of Benzene with 1-Dodecene
Benzene: 1-dodecene Mole Ration: as indicated
1-dodecene:Catalyst Weight Ratio: as indicated
Temperature: 80.1° C (B.P. of Benzene)
Duration of Run: 1, 24 Hours
Catalyst: Al$^{3+}$- and Cr$^{3+}$-exchanged Hectorite as indicated

| Ex. | Exchangeable Cation on Hectorite | 1-dodecene to Catalyst Wt. Ratio | Benzene to 1-dodecene Mole Ratio | % Conversion of 1-dodecene 1 Hr. | 24 Hr. |
|---|---|---|---|---|---|
| 49 | Cr$^{3+}$ | 10:1 | 10:1 | 99.6 | — |
| 50 | Cr$^{3+}$ | 20:1 | 10:1 | 98.4 | — |
| 51 | Cr$^{3+}$ | 40:1 | 10:1 | 70.1 | — |
| 52 | Cr$^{3+}$ | 100:1 | 10:1 | 43.7 | 83.8 |
| 53 | Al$^{3+}$ | 10:1 | 10:1 | 97.0 | — |
| 54 | Al$^{3+}$ | 20:1 | 10:1 | 98.2 | — |
| 55 | Al$^{3+}$ | 40:1 | 10:1 | 82.1 | 99.0 |
| 56 | Al$^{3+}$ | 50:1 | 5:1 | 55.2 | 90.2 |
| 57 | Al$^{3+}$ | 100:1 | 10:1 | 34.2 | 78.0 |
| 58 | Al$^{3+}$ | 100:1 | 5:1 | 18.9 | 71.6 |
| 59 | Al$^{3+}$ | 100:1 | 20:1 | 29.6 | 67.1 |

EXAMPLE 60

A synthetic saponite-type clay was prepared by reacting at a temperature of 300° C in a Ag-lined stainless steel autoclave under the autogenous water vapor pressure created in the autoclave for 24 hours a composition having the molar formula:

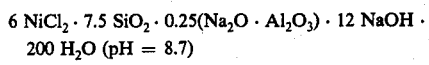
6 NiCl$_2$ · 7.5 SiO$_2$ · 0.25(Na$_2$O · Al$_2$O$_3$) · 12 NaOH · 200 H$_2$O (pH = 8.7)

The product obtained, after drying at 105° C had X-ray diffraction peaks at 12.5 A and 1.523 A which indicates that the product was a well crystallized trioctahedral 2:1 layer-lattice saponite-type clay. The expected formula for this nickeliferous saponite is:

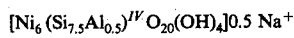
[Ni$_6$ (Si$_{7.5}$Al$_{0.5}$)$^{IV}$O$_{20}$(OH)$_4$]0.5 Na$^+$

This saponite-type clay was exchanged to the Al$^{3+}$-form as follows: the dried saponite-type clay was mixed into an aqueous AlCl$_3$ solution at a concentration of 300 milliequivalents of Al$^{3+}$ per 100 grams of clay. The mixture was allowed to stand for approximately 20 hours before it was filtered. The filter cake was re-dispersed in 500 - 750 ml. of deionized water followed by filtration for a total of 2 successive washings. Thereafter another washing was undertaken substituting methanol for the deionized water. The Al$^{3+}$-cation exchanged saponite-type clay was then air dried for 20 hours at room temperature followed by oven drying at 105° C for 2 hours. The clay obtained by this process was very fine and needed no grinding.

The Al$^{3+}$-exchanged saponite-type clay was evaluated as follows: 1 gram of the clay and 200 - 500 ml. of benzene were refluxed in a round bottom flask equipped with a Dean-Stark tube attached to remove, azeotropically, sorbed water from the clay. After 2 - 4 hours the tube was removed and the reflux condenser rinsed with methanol and air dried to remove any residual moisture trapped in the condenser. 10 grams of 1-dodecene were then added to the flask and the mixture refluxed with stirring.

After 1 hour a sample was taken and analyzed by gas chromatographic analysis. 79% of the 1-dodecene was converted to dodecylbenzenes.

EXAMPLE 61

Another synthetic saponite-type clay was prepared by the process of Example 60 at a temperature of 350° C starting with a composition having the molar formula:

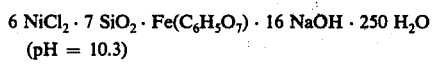
6 NiCl$_2$ · 7 SiO$_2$ · Fe(C$_6$H$_5$O$_7$) · 16 NaOH · 250 H$_2$O
(pH = 10.3)

The product obtained after drying at 105° C had X-ray diffraction peaks at 13.0 A and 1.534 A° which indicates that the product was a well crystallized trioctahedral 2:1 layer-lattice saponite-type clay. The expected formula for this clay is:

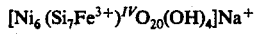
[Ni$_6$ (Si$_7$Fe$^{3+}$)$^{IV}$O$_{20}$(OH)$_4$]Na$^+$

This saponite-type clay was exchanged to the Al$^{3+}$-form and evaluated as in Example 60. 95.5% of the 1-dodecene was converted to dodecylbenzenes in 1 hour.

EXAMPLE 62

A synthetic saponite-type clay was prepared by the process of Example 60 at a temperature of 350° C starting with a composition having the molar formula:

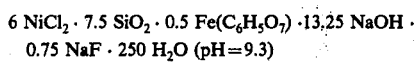
6 NiCl$_2$ · 7.5 SiO$_2$ · 0.5 Fe(C$_6$H$_5$O$_7$) · 13.25 NaOH · 0.75 NaF · 250 H$_2$O (pH=9.3)

The product obtained after drying at 105° C had X-ray diffraction peaks at 13.5 A and 1.524 A which indicates that the product was a well crystallized trioctahedral 2:1 layer-lattice saponite-type clay. The expected formula for this clay is:

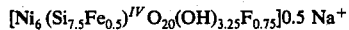
[Ni$_6$ (Si$_{7.5}$Fe$_{0.5}$)$^{IV}$O$_{20}$(OH)$_{3.25}$F$_{0.75}$]0.5 Na$^+$ This saponite-type clay was exchanged to the Al$^{3+}$-form and evaluated as in Example 60. 23.2% of the 1-dodecene was converted to dodecylbenzenes in 1 hour.

EXAMPLE 63

A synthetic saponite-type clay was prepared by the process of Example 60 at a temperature of 350° C, synthesis time 48-hours, starting with a composition having the molar formula:

$6CoCl_2 \cdot 7SiO_2 \cdot AlCl_3 \cdot 16\ NaOH \cdot 250\ H_2O$
(pH = 12.5)

The product obtained after drying at 105° C had x-ray diffraction peaks at 12.5 A and 1.538 A which indicates that the product was a well crystallized trioctahedral 2:1 layer-lattice saponite-type clay. The expected formula for this clay is:

$[Co_6(Si_7Al)^{IV}O_{20}(OH)_4]Na^+$

This saponite-type clay was exchanged to the $Al^{3+}$-form and evaluated as in Example 60. 33.5% of the 1-dodecene was converted to dodecylbenzenes in 20 hours.

EXAMPLE 64

A synthetic saponite-type clay was prepared by the process of Example 63 starting with a composition having the molar formula:

$6NiCl_2 \cdot 7SiO_2 \cdot CrCl_3 \cdot 16\ NaOH \cdot 250\ H_2O$
(pH = 11.3)

The product obtained after drying at 105° C had x-ray diffraction peaks at 11 A and 1.525 A which indicates that the product was a trioctahedral 2:1 layer-lattice saponite-type clay. The expected formula for this clay is:

$[Ni_6(Si_7Cr)^{IV}O_{20}(OH)_4]Na^+$

This saponite-type clay was exchanged to the $Al^{3+}$-form and evaluated as in Example 60. 18% of the 1-dodecene was converted to dodecylbenzenes in 20 hours.

EXAMPLE 65

The procedure of Example 60 is repeated wherein the saponite-type clay is exchanged with the following metallic cations: $Cr^{3+}$, $In^{3+}$, $Fe^{3+}$, $Ga^{3+}$, $Mn^{2+}$, $Co^{3+}$, $Co^{2+}$, $Ni^{2+}$, $Cu^{2+}$, $Ag^+$, $Be^{2+}$, $Mg^{2+}$, $La^{3+}$, $Ce^{3+}$, $Pd^{2+}$ and mixtures thereof.

EXAMPLE 66

A synthetic hectorite-type clay was prepared by reacting at a temperature of 350° C in a Ag-lined stainless steel autoclave under the autogenous water vapor pressure created in the autoclave for 48 hours a composition having the molar formula:

$5.32\ NiCl_2 \cdot 0.68\ LiCl \cdot 8SiO_2 \cdot 12\ NaOH \cdot 250\ H_2O$
(pH = 11.5)

The product obtained, after drying at 105° C, had x-ray diffraction peaks at 12.5 A and 1.517 A which indicates that the product was a well crystallized hectorite-type clay. The expected formula for this nickelferous hectorite is:

$[(Ni^{+2}_{5.32}Li^{+1}_{0.68})^{VI}(Si_8)^{IV}O_{20}(OH)_4]0.68\ Na^+$

This synthetic hectorite-type clay mineral was exchanged to the $Al^{3+}$-form and evaluated as in Example 60. After one hour a sample was taken and analyzed by gas chromatographic analysis. 21.1% of the 1-dodecene was converted to dodecylbenzene and 9.8% of the 1-dodecene was converted to heavy alkylate. After 24 hours another sample was taken and analyzed. 67.5% of the 1-dodecene was converted to dodecylbenzene and 15.8 % of the 1-dodecene was converted to heavy alkylate.

EXAMPLE 67

A synthetic hectorite-type clay was prepared by the process of Example 66 starting with a composition having the molar formula:

$5.32\ CoCl_2 \cdot 0.68\ LiCl \cdot 8\ SiO_2 \cdot 12\ NaOH \cdot 250\ H_2O$
(pH 32 12.1)

The product obtained, after drying at 105° C, had x-ray diffraction peaks at 12.7 A and 1.522 A which indicates that the product was a well crystallized hectorite-type clay. The expected formula for this cobaltiferous hectorite is:

$[(Co^{2+}_{5.32}Li^+_{0.68})^{VI}(Si_8)^{IV}O_{20}(OH)_4]0.68Na^+$

This synthetic hectorite-type clay was exchanged to the $Al^{3+}$-form and evaluated as in Example 60. 48.1% of the 1-dodecene was converted to dodecylbenzene and 8.7% of the 1-dodecene was converted to heavy alkylate after 24 hours refluxing.

EXAMPLE 68

The procedures of Example 66 are repeated wherein the hectorite-type clay is exchanged with the following metallic cations: $Cr^{3+}$, $In^{3+}$, $Fe^{3+}$, $Ga^{3+}$, $Mn^{2+}$, $Co^{3+}$, $Co^{2+}$, $Ni^{2+}$, $Cu^{2+}$, $Ag^{30}$, $Be^{2+}$, $Mg^{2+}$, $La^{3+}$, $Ce^{3+}$, $Pd^{2+}$, $Pt^{2+}$, and mixtures thereof.

Thus these catalysts have the following structural formula:

$(Ni^{+2}_{5.32}Li^+_{0.68})^{VI}(Si_8)^{IV}O_{20}(OH)_4](0.68/z)\ R^z$ where $R^z$ = $Cr^{3+}$, $In^{3+}$, $Fe^{3+}$, $Ga^{3+}$, $Mn^{2+}$, $Co^{3+}$, $Co^{2+}$, $Ni^{2+}$, $Cu^{2+}$, $Ag+$, $Be^{2+}$, $Mg^{2+}$, $La^{3+}$, $Ce^{3+}$, $Pd^{2+}$, $Pt^{2+}$, and mixtures thereof.

EXAMPLE 69

The procedures of Example 66 are repeated wherein the autoclave feed composition has the molar formula:

$2.66\ Ni\ Cl_2 \cdot 2.66\ CoCl_2 \cdot 0.68\ Li\ F \cdot 8\ SiO_2 \cdot 12\ NaOH \cdot 250\ N_2O$ The formula for this nickeliferous-cobaltiferous hectorite-type clay is:

$[(Ni^{2+}_{2.66}Co^{2+}_{2.66}Li^+_{0.68})^{VI}(Si_8)^{IV}O_{20}(OH)_{3.32}F_{0.68}]0.68\ Na+$

The formula for the $Al^{3+}$-exchanged catalyst is:

$[(Ni^{2+}_{2.66}Co^{2+}_{2.66}Li^+_{0.68})^{VI}(Si_8)^{IV}O_{20}(OH)_{3.32}F_{0.68}]0.227\ Al^{3+}$

It will be understood that while I have explained the invention with the aid of specific examples, nevertheless considerable variation is possible in choice of raw materials, proportions, processing conditions and the like, within the broad scope of the invention as set forth in the claims which follow. Thus, for example, my inventive catalyst may be used simultaneously with other catalytic materials so as to suit particular conditions and circumstances.

I claim:

1. A catalyst comprising a synthetic trioctahedral 2:1 layer-lattice smectite-type clay mineral containing a metallic cation having a Pauling electronegativity greater than 1.0 in cation exchange positions on the surface of said mineral, said mineral having the structural formula:

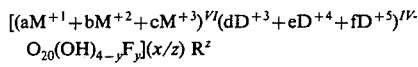

where
$11 \leq a + 2b + 3c \leq 12.3$
$31 \leq 3d + 4e + 5f \leq 32$
$43 \leq a + 2b + 3c + 3d + 4e + 5f \leq 43.67$
$x = 44 - (a + 2b + 3c + 3d + 4e + 5f)$
$0 \leq y \leq 4$
$0 \leq a \leq 1$
$5 \leq b \leq 6$
$0 \leq c \leq 0.3$
$0 \leq d \leq 1$
$7 \leq e \leq 8$
$0 \leq f \leq 0.4$ provided that when $a=0$, then either: (1) $f>0$; or (2) $c>0$ and $M^{+3}$ and $D^{+3}$ are not $Al^{+3}$ when $M^{+2}$ is 100 mole percent $Mg^{+2}$, and where the cations M are in the octahedral layer and have an ionic radius not greater than 0.75 A, the cations D are in the two outer tetrahedral layers and have an ionic radius not greater than 0.64 A, and R is at least one of said metallic cations having a Pauling electronegativity greater than 1.0 of valence z.

2. The catalyst of claim 1 wherein $0 < a \leq 1$ and $0 < d \leq 1$.

3. The catalyst of claim 1 wherein $0 < a \leq 1$ and $0 < f \leq 0.4$.

4. The catalyst of claim 1 wherein $0 < a \leq 1$ and $0 < c \leq 0.3$.

5. The catalyst of claim 1 wherein $a=0$ and $0 < f \leq 0.4$.

6. The catalyst of claim 1 wherein said R is selected from the group consisting of $Al^{3+}$, $Cr^{3+}$, $Ga^{3+}$, $In^{3+}$, $Mn^{2+}$, $Fe^{3+}$, $Co^{3+}$, $Co^{2+}$, $Ni^{2+}$, $Cu^{2+}$, $Ag^+$, $Be^{2+}$, $Mg^{2+}$, $La^{3+}$, $Ce^{3+}$, $Pd^{2+}$, $Pt^{2+}$, and mixtures thereof.

7. The catalyst of claim 6 wherein $0 \leq a \leq 1$ and $0 \leq d \leq 1$.

8. The catalyst of claim 6 wherein $0 < a \leq 1$ and $0 < f \leq 0.4$.

9. The catalyst of claim 6 wherein $0 < a \leq 1$ and $0 < c \leq 0.3$.

10. The catalyst of claim 6 wherein $a=0$ and $0 < f \leq 0.4$.

11. The catalyst of claim 1 wherein R is selected from the group consisting of $In^{+3}$, $Pd^{+2}$, $Pt^{+2}$, the rare earths, and mixtures thereof.

12. The catalyst of claim 11 wherein $0 < a \leq 1$ and $0 < d \leq 1$.

13. The catalyst of claim 11 wherein $0 < a \leq 1$ and $0 < f \leq 0.4$.

14. The catalyst of claim 11 wherein $0 < a \leq 1$ and $0 < c \leq 0.3$.

15. The catalyst of claim 11 wherein $a=0$ and $0 < f \leq 0.4$.

16. The catalyst of claim 1 wherein M is selected from the group consisting of $Li^+$, $Mg^{2+}$, $Ni^{2+}$, $Co^{2+}$, $Zn^{2+}$, $Cu^{2+}$, $Mn^{2+}$, $Al^{3+}$, $Cr^{3+}$, and mixtures thereof, and D is selected from the group consisting of $Al^{3+}$, $Cr^{3+}$, $Fe^{3+}$, $Si^{+4}$, $Ge^{+4}$, $P^{+5}$, $V^{+5}$, and mixtures thereof.

17. The catalyst of claim 16 wherein $0 < a \leq 1$ and $0 < d \leq 1$.

18. The catalyst of claim 16 wherein $0 < a = 1$ and $0 < f \leq 0.4$.

19. The catalyst of claim 16 wherein $0 < a \leq 1$ and $0 < c \leq 0.3$.

20. The catalyst of claim 16 wherein $a=0$ and $0 < f \leq 0.4$.

21. The catalyst of claim 1 wherein M is selected from the group consisting of $Li^+$, $Mg^{+2}$, $Ni^{+2}$, $Co^{+2}$, $Zn^{+2}$, $Cu^{+2}$, $Mn^{+2}$, $Al^{+3}$, $Cr^{+3}$, and mixtures thereof, D is selected from the group consisting of $Al^{+3}$, $Cr^{+3}$, $Fe^{+3}$, $Si^{+4}$, $Ge^{+4}$, $P^{+5}$, $V^{+5}$, and mixtures thereof, and R is selected from the group consisting of $Al^{+3}$, $Cr^{+3}$, $Ga^{+3}$, $In^{+3}$, $Mn^{+2}$, $Fe^{+3}$, $Co^{+3}$, $Co^{+2}$, $Ni^{+2}$, $Cu^{+2}$, $Ag+$, $Be^{+2}$, $Mg^{+2}$, $La+3$, $Ce^{+3}$, $Pd^{+2}$, $Pt^{+2}$, and mixtures thereof.

22. The catalyst of claim 21 wherein $0 < a \leq 1$ and $0 < d \leq 1$.

23. The catalyst of claim 21 wherein $0 < a \leq 1$ and $0 < f \leq 0.4$.

24. The catalyst of claim 21 wherein $0 < a \leq 1$ and $0 < c \leq 0.3$.

25. The catalyst of claim 21 wherein $a=0$ and $0 < f \leq 0.4$.

26. The catalyst of claim 1 wherein M is selected from the group consisting of $Li^+$, $Mg^{+2}$, $Ni^{+2}$, $Co^{+2}$, $Zn^{+2}$, $Cu^{+2}$, $Mn^{+2}$, $Al^{+3}$, $Cr^{+3}$, and mixtures thereof, D is selected from the group consisting of $Al^{+3}$, $Cr^{+3}$, $Fe^{+3}$, $Si^{+4}$, $Ge^{+4}$, $P^{+5}$, $V^{+5}$, and mixtures thereof, and R is selected from the group consisting of $In^{+3}$, $Pd^{+2}$, $Pt^{+2}$, the rare earths, and mixtures thereof.

27. The catalyst of claim 26 wherein $0 < a \leq 1$ and $0 < d \leq 1$.

28. The catalyst of claim 26 wherein $0 < a \leq 1$ and $0 < f \leq 0.4$.

29. The catalyst of claim 26 wherein $0 < a \leq 1$ and $0 < c \leq 0.3$.

30. The catalyst of claim 26 wherein $a=0$ and $0 < f \leq 0.4$.

* * * * *

UNITED STATES PATENT OFFICE
CERTIFICATE OF CORRECTION

Patent No. 4,075,126      Dated February 21, 1978

Inventor(s) GEORGE E. STRIDDE

It is certified that error appears in the above-identified patent and that said Letters Patent are hereby corrected as shown below:

Claim 7, lines 50 and 51 - "$0 \leq a \leq 1$ and $0 \leq d \leq 1$" should read -- $0 < a \leq 1$ and $0 < d \leq 1$ --.

Claim 18, line 19 - "$0 < a = 1$" should read -- $0 < a \leq 1$ --.

Claim 21, line 31 - "Ag+" should read -- $Ag^+$ --.

Claim 21, line 32 - "La+3" should read -- $La^{+3}$ --.

Signed and Sealed this Twentieth Day of June 1978

[SEAL]

Attest:

RUTH C. MASON
*Attesting Officer*

DONALD W. BANNER
*Commissioner of Patents and Trademarks*